(12) United States Patent
Thornton

(10) Patent No.: US 7,909,035 B2
(45) Date of Patent: Mar. 22, 2011

(54) MULTI-CHAMBER MASK AND METHOD OF FORMING THE SAME

(75) Inventor: W. Keith Thornton, Dallas, TX (US)

(73) Assignee: AirWay Technologies, LLC, Dallas, TX (US)

( * ) Notice: Subject to any disclaimer, the term of this patent is extended or adjusted under 35 U.S.C. 154(b) by 1165 days.

(21) Appl. No.: 11/428,933

(22) Filed: Jul. 6, 2006

(65) Prior Publication Data

US 2007/0006879 A1     Jan. 11, 2007

Related U.S. Application Data

(60) Provisional application No. 60/698,181, filed on Jul. 11, 2005.

(51) Int. Cl.
*A62B 18/02* (2006.01)

(52) U.S. Cl. ......... 128/206.21; 128/206.24; 128/205.25; 128/206.28

(58) Field of Classification Search ............. 128/201.22, 128/201.29, 205.25, 206.21–206.24, 206.28, 128/206.29, 207.11–207.13; 264/241; 156/322
See application file for complete search history.

(56) References Cited

U.S. PATENT DOCUMENTS

| | | | |
|---|---|---|---|
| 339,334 A | 4/1886 | Searle | |
| 690,663 A | 1/1902 | Pratt | |
| 746,869 A | 12/1903 | Moulton | |
| 774,446 A | 11/1904 | Moulton | |
| 781,516 A | 1/1905 | Guthrie, Jr. | |
| 885,196 A | 4/1908 | Steil | |
| 893,213 A | 7/1908 | Whiteway | |
| 996,783 A | 7/1911 | Moreau | |
| 1,483,694 A | 2/1924 | Stukey | |
| 1,675,202 A | 6/1928 | Warne | |

(Continued)

FOREIGN PATENT DOCUMENTS

DE         156627       12/1904

(Continued)

OTHER PUBLICATIONS

PCT, Notification of Transmittal of the International Search Report and the Written Opinion of the International Searching Authority, or the Declaration, PCT/US06/26622, 11 pages, Date Mailed: Feb. 21, 2007.

(Continued)

*Primary Examiner* — Justine R Yu
*Assistant Examiner* — Colin Stuart
(74) *Attorney, Agent, or Firm* — Baker Botts L.L.P.

(57) ABSTRACT

A multi-chamber mask includes a shell and a partition. The shell is adapted to cover portions of a user's face including the mouth and at least portions of the nose including the nostrils, the shell adapted to contact the face surrounding the covered portions of the face to substantially prevent gas from escaping between the shell and the contacted portions of the user's face, and the shell is adapted to couple to a gas supply source. The partition is coupled to the shell and cooperates with the shell to define a first chamber and a second chamber, the first chamber adapted to be positioned proximate the user's nose to direct inflow of gas from the gas supply source to the user's nasal passages, the second chamber adapted to be positioned proximate the user's mouth, the partition adapted to restrict flow of gas between the first and the second chamber.

41 Claims, 5 Drawing Sheets

U.S. PATENT DOCUMENTS

| | | | | |
|---|---|---|---|---|
| 1,679,748 | A | 8/1928 | Stratton | |
| 2,178,128 | A | 10/1939 | Waite | 128/136 |
| 2,383,649 | A | 8/1945 | Heidbrink | 128/142 |
| 2,424,533 | A | 7/1947 | Faires | 128/136 |
| 2,505,028 | A | 4/1950 | Boeger | 128/215 |
| 2,521,084 | A | 9/1950 | Oberto | 128/141 |
| 2,574,623 | A | 11/1951 | Clyde | 128/136 |
| 2,627,268 | A | 2/1953 | Leppich | 128/136 |
| 2,671,446 | A | 3/1954 | Mann | 128/163 |
| 2,867,212 | A | 1/1959 | Nunn, Jr. | 128/136 |
| 2,882,893 | A | 4/1959 | Godfroy | 128/136 |
| 2,917,045 | A | 12/1959 | Schildknecht et al. | 128/141 |
| 2,977,636 | A | 4/1961 | McGuire | 18/58.7 |
| 3,037,501 | A | 6/1962 | Miller | 128/141 |
| 3,330,274 | A | 7/1967 | Bennett | 128/146.7 |
| 3,658,058 | A | 4/1972 | Neidhart et al. | 128/147 |
| 3,695,265 | A | 10/1972 | Brevik | 128/146.2 |
| 3,845,768 | A | 11/1974 | Garrahan | 128/142.7 |
| 4,050,457 | A | 9/1977 | Davidson | 128/145.5 |
| 4,233,972 | A | 11/1980 | Hauff et al. | 128/205.12 |
| 4,258,710 | A * | 3/1981 | Reber | 128/204.18 |
| 4,289,127 | A | 9/1981 | Nelson | 128/207.14 |
| 4,294,243 | A | 10/1981 | Ernsting et al. | 128/201.18 |
| 4,345,592 | A | 8/1982 | Giorgini et al. | 128/204.26 |
| 4,345,593 | A | 8/1982 | Sullivan | 128/204.26 |
| 4,392,490 | A | 7/1983 | Mattingly et al. | 128/202.27 |
| 4,397,701 | A | 8/1983 | Johnson et al. | 156/62 |
| 4,454,090 | A | 6/1984 | Saumell | 264/154 |
| 4,470,413 | A | 9/1984 | Warncke | 128/201.18 |
| 4,655,213 | A | 4/1987 | Rapoport et al. | 128/205.25 |
| 4,706,683 | A | 11/1987 | Chilton et al. | 128/654 |
| 4,784,123 | A | 11/1988 | Robeson | 128/90 |
| 4,858,605 | A | 8/1989 | Levy | 128/203.11 |
| 4,858,606 | A | 8/1989 | Hamlin | 128/204.29 |
| 4,862,903 | A | 9/1989 | Campbell | 128/861 |
| 4,870,962 | A | 10/1989 | Sitnik | 128/205.13 |
| 4,886,056 | A | 12/1989 | Simpson | 128/201.25 |
| 4,906,234 | A | 3/1990 | Voychehovski | 604/79 |
| 4,919,128 | A | 4/1990 | Kopala et al. | 128/207.18 |
| 4,941,212 | A | 7/1990 | Liff | 2/206 |
| 5,042,478 | A | 8/1991 | Kopala et al. | 128/207.18 |
| 5,062,421 | A | 11/1991 | Burns et al. | 128/205.27 |
| 5,065,756 | A | 11/1991 | Rapoport | 128/204.18 |
| 5,066,231 | A | 11/1991 | Oxman et al. | 433/214 |
| 5,193,532 | A | 3/1993 | Moa et al. | 128/204.25 |
| 5,233,978 | A | 8/1993 | Callaway | 128/205.25 |
| 5,243,971 | A | 9/1993 | Sullivan et al. | 128/205.25 |
| 5,243,972 | A * | 9/1993 | Huang | 128/205.25 |
| 5,245,995 | A | 9/1993 | Sullivan et al. | 128/204.23 |
| 5,265,595 | A * | 11/1993 | Rudolph | 128/204.18 |
| 5,267,557 | A | 12/1993 | Her-Mou | 128/206.21 |
| 5,392,773 | A | 2/1995 | Bertrand | 128/206.11 |
| 5,456,264 | A | 10/1995 | Series et al. | 128/725 |
| 5,458,137 | A | 10/1995 | Axe et al. | 128/204.23 |
| 5,474,060 | A * | 12/1995 | Evans | 128/204.22 |
| 5,477,850 | A | 12/1995 | Zegler et al. | 128/202.11 |
| 5,503,146 | A | 4/1996 | Froehlich et al. | 128/204.23 |
| 5,517,983 | A | 5/1996 | Deighan et al. | 128/204.23 |
| 5,537,994 | A | 7/1996 | Thornton | 128/204.18 |
| 5,537,999 | A | 7/1996 | Dearman et al. | 128/205.25 |
| 5,538,000 | A | 7/1996 | Rudolph | 128/205.25 |
| 5,538,014 | A | 7/1996 | Wilson et al. | 128/863 |
| 5,540,223 | A | 7/1996 | Starr et al. | 128/205.25 |
| 5,551,419 | A | 9/1996 | Froehlich et al. | 128/204.23 |
| 5,558,090 | A | 9/1996 | James | 128/207.18 |
| RE35,339 | E | 10/1996 | Rapoport | 128/204.18 |
| 5,560,354 | A | 10/1996 | Berthon-Jones et al. | 128/205.25 |
| 5,592,935 | A | 1/1997 | Elstran et al. | 128/205.25 |
| 5,611,485 | A | 3/1997 | Davis | 239/8 |
| 5,657,751 | A | 8/1997 | Karr, Jr. | 128/205.18 |
| 5,657,752 | A | 8/1997 | Landis et al. | 128/207.13 |
| 5,662,101 | A | 9/1997 | Ogden et al. | 128/205.25 |
| 5,676,133 | A | 10/1997 | Hickle et al. | 128/205.12 |
| 5,687,715 | A | 11/1997 | Landis et al. | 128/207.18 |
| 5,713,349 | A | 2/1998 | Keaney | 128/204.23 |
| 5,718,244 | A | 2/1998 | Thornton | 128/864 |
| 5,718,500 | A | 2/1998 | Vinci guerra et al. | 2/431 |
| 5,720,280 | A | 2/1998 | Elstran et al. | 128/205.25 |
| 5,724,965 | A | 3/1998 | Handke et al. | 128/207.13 |
| 5,746,201 | A | 5/1998 | Kidd | 128/206.24 |
| 5,752,510 | A | 5/1998 | Goldstein | 128/207.18 |
| 5,807,100 | A | 9/1998 | Thornton | 433/48 |
| 5,810,749 | A | 9/1998 | Maas | 602/6 |
| 5,832,918 | A | 11/1998 | Pantino | 128/205.25 |
| 5,846,082 | A | 12/1998 | Thornton | 433/215 |
| 5,887,587 | A | 3/1999 | Groenke | 128/207.13 |
| 5,954,048 | A | 9/1999 | Thornton | 128/201.18 |
| 5,983,892 | A | 11/1999 | Thornton | 128/201.26 |
| 5,988,166 | A | 11/1999 | Hayek | 128/205.26 |
| 6,012,455 | A | 1/2000 | Goldstein | 128/207.18 |
| 6,083,442 | A | 7/2000 | Gabilly | 264/163 |
| 6,119,694 | A | 9/2000 | Correa et al. | 128/207.13 |
| 6,123,071 | A | 9/2000 | Berthon-Jones et al. | 128/204.18 |
| 6,209,542 | B1 | 4/2001 | Thornton | 128/206.29 |
| 6,263,871 | B1 | 7/2001 | Brown et al. | 128/200.29 |
| D448,473 | S | 9/2001 | Barnett et al. | D24/110.1 |
| 6,374,824 | B1 | 4/2002 | Thornton | 128/201.26 |
| 6,405,729 | B1 | 6/2002 | Thornton | 128/848 |
| 6,412,488 | B1 | 7/2002 | Barnett et al. | 128/207.13 |
| 6,464,924 | B1 | 10/2002 | Thornton | 264/331.12 |
| 6,494,206 | B1 | 12/2002 | Bergamaschi et al. | 128/206.24 |
| 6,571,798 | B1 | 6/2003 | Thornton | 128/206.21 |
| 6,645,413 | B2 | 11/2003 | Jacobs | 264/222 |
| 6,675,802 | B1 | 1/2004 | Thornton | 128/206.29 |
| 6,758,212 | B2 * | 7/2004 | Swann | 128/201.25 |
| 6,857,428 | B2 | 2/2005 | Thornton | 128/206.21 |
| 6,877,513 | B2 | 4/2005 | Scarberry et al. | 128/848 |
| 7,077,138 | B2 | 7/2006 | Bateman et al. | 128/206.14 |
| 2002/0129818 | A1 | 9/2002 | Morgan et al. | 128/206.26 |
| 2002/0139366 | A1* | 10/2002 | Gaschke | 128/201.13 |
| 2004/0079374 | A1* | 4/2004 | Thornton | 128/206.21 |
| 2004/0226563 | A1* | 11/2004 | Xu et al. | 128/206.21 |
| 2004/0237965 | A1 | 12/2004 | Bibi et al. | 128/206.29 |
| 2005/0016544 | A1 | 1/2005 | Thornton | 128/207.18 |
| 2006/0005837 | A1 | 1/2006 | Thornton | 128/205.25 |
| 2006/0124131 | A1 | 6/2006 | Chandran et al. | 128/206.28 |

FOREIGN PATENT DOCUMENTS

| | | |
|---|---|---|
| DE | 35 43 931 A1 | 6/1987 |
| DE | 37 07 952 A1 | 9/1988 |
| DE | 37 19 009 A1 | 12/1988 |
| DE | 44 38 512 A1 | 5/1996 |
| DE | 198 46 686 A1 | 7/1999 |
| FR | 2 658 725 A1 | 8/1991 |
| FR | 2 731 624 A1 | 9/1996 |
| FR | 2731624 | 9/1996 |
| WO | WO 98/20924 | 5/1998 |
| WO | WO 98/46177 | 10/1998 |

OTHER PUBLICATIONS

Mayo Clinic Health Letter; Reliable Information for a Healthier Life; *Snoring: Laser Surgery Joins Battle to Restore Peace and Quiet*; vol. 13, No. 7, 8 pages, Jul. 1995.

Schmidt-Nowara, et al.; An American Sleep Disorders Association Review; *Oral Appliances for the Treatment of Snoring and Obstructive Sleep Apnea: A Review*; pp. 501-510, 1995.

CPAP-PRO—Introducing A New Comfort Level for CPAP Users brochure, 2 pages.

"Donning the Mask," Dräger: X-plore 5500.2006.Dräger Safety, http://www.draeger-usa.com/ST/internet/pdf/US/protection/ AnlegiPO_X-plore_5500_US.pdf, 2 pages, Accessed Sep. 14, 2006.

European Patent Office Communication, Application No. 03 809 555.0—1257, Applicant: W. Keith Thornton, 4 pages, dated Aug. 7, 2009.

Canadian Intellectual Property Office, Application No. 2,502,280, Applicant: W. Keith Thornton, 3 pages, dated Feb. 23, 2010.

* cited by examiner

MULTI-CHAMBER MASK AND METHOD OF FORMING THE SAME

RELATED APPLICATION

This application claims the benefit under 35 U.S.C. §119(e) of U.S. Provisional Application Ser. No. 60/698,181 filed Jul. 11, 2005.

TECHNICAL FIELD

This invention relates generally to masks for use in medical and other clinical applications, and more particularly to a multi-chamber mask and method of forming the same.

BACKGROUND

Many people experience breathing problems on a recurring basis, which often results in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included face masks, nose masks, or nasal inserts that help deliver air to the user's nose at positive pressure. These devices help force open the user's breathing passage and thereby improve the user's breathing. However, previous devices have often provided an inadequate fit and have often failed to adequately prevent leakage. In addition, previous devices have caused discomfort for users and thus have been poorly suited for treating breathing problems such as sleep disordered breathing.

SUMMARY OF THE INVENTION

According to one embodiment, a multi-chamber mask includes a shell and a partition. The shell is adapted to cover portions of a user's face including the user's mouth and at least portions of the user's nose including the nostrils, the shell adapted to contact the user's face surrounding the covered portions of the user's face to substantially prevent gas from escaping between the shell and the contacted portions of the user's face, and the shell is adapted to couple to a gas supply source. The partition is coupled to the shell and cooperates with the shell to define a first chamber and a second chamber, the first chamber adapted to be positioned proximate the user's nose to direct inflow of gas from the gas supply source to the user's nasal passages, the second chamber adapted to be positioned proximate the user's mouth to restrict outflow of gas from the user's mouth in response to inflow of gas from the gas supply source to the user's nasal passages, the partition adapted to restrict flow of gas between the first and the second chamber.

According to another embodiment a method of forming a multi-chamber mask includes providing a first layer of deformable material covering portions of a facial surface, the facial surface representing physical features of a user's face, the covered portions of the facial surface portions corresponding to the user's mouth and at least a portion of the user's nose including the nostrils. One or more openings are provided in the first layer of deformable material corresponding to the user's mouth and nostrils. One or more spacers are provided covering at least a portion of the facial surface corresponding to the user's mouth. A second layer of deformable material is provided over the one or more spacers and at least a portion of the first layer. A partition is provided between the first and second layers of deformable material adapted to cooperate with the first and second layers of deformable material to define a first chamber and a second chamber, the first chamber adapted to be positioned proximate the user's nose to direct inflow of gas from a gas supply source to the user's nasal passages, the second chamber adapted to be positioned proximate the user's mouth to restrict outflow of gas from the user's mouth in response to inflow of gas from the gas supply source to the user's nasal passages, the partition adapted to restrict flow of gas between the first and the second chamber. The first layer of deformable material is coupled to the second layer of deformable material, with the partition between the first and second layers of deformable material, to form the multi-chamber mask.

Certain embodiments may provide one or more technical advantages. For example, in certain embodiments, a single multi-chamber mask allows a gas to flow to the nasal passages, while at the same time reducing or preventing the gas form flowing to the mouth. Certain embodiments may allow the mask to connect to an oral appliance or provide access to an oral appliance through an opening in the mask. Certain embodiments may provide a custom-fitted mask that conforms substantially optimally to a user's unique facial structure and features. Certain embodiments may provide improved fit, increased comfort, reduced leakage, and improved performance, whether for treating sleep disordered breathing, for administering anesthesia, or for any other suitable purpose for which the multi-chamber mask is used. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and its advantages, reference is now made to the following description, taken in conjunction with the accompanying drawings, in which.

DESCRIPTION OF EXAMPLE EMBODIMENTS

Figure 1A:
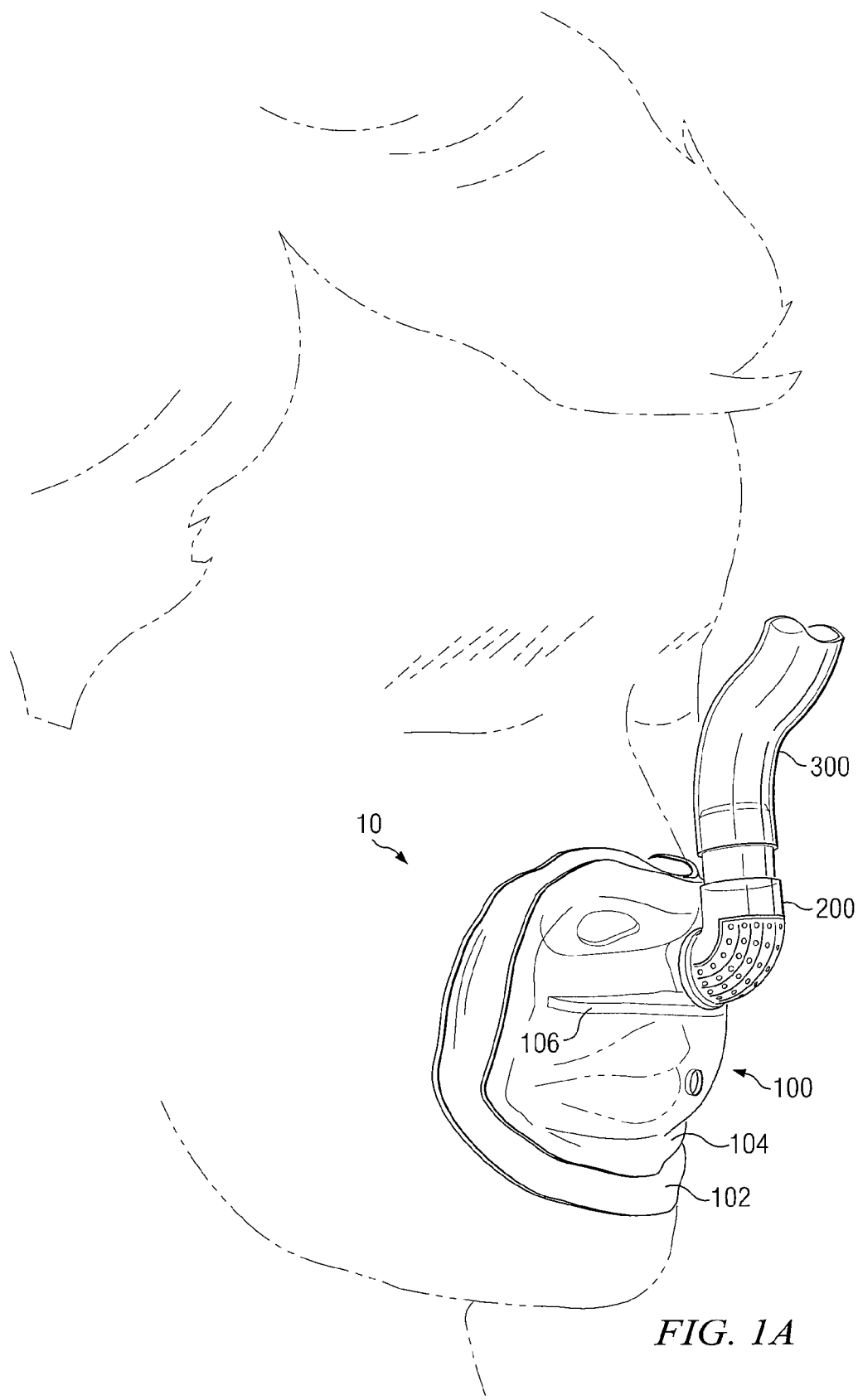
FIGS. 1A and 1B illustrate an example system for improving a user's breathing including an example multi-chamber mask.
Figure 1B:
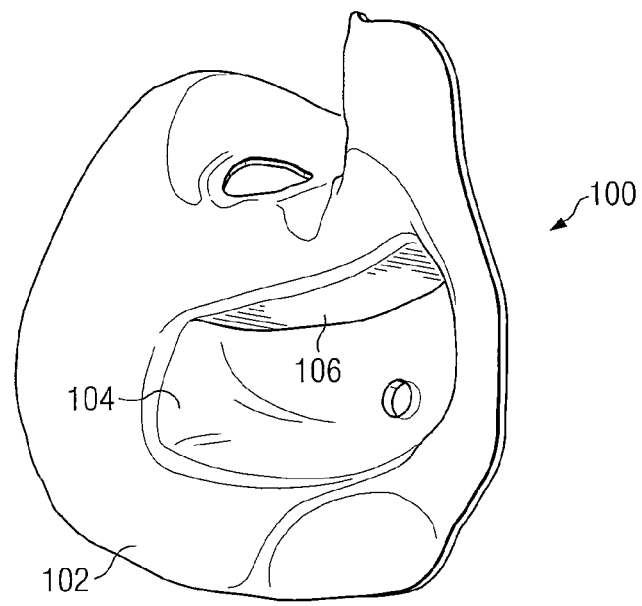

FIGS. 1A and 1B illustrate an example system 10 for improving a user's breathing. In certain embodiments, system 10 includes an example multi-chamber mask 100, coupled through an example fitting 200 to an example gas supply source 300. In operation, system 10 may be used to administer air, oxygen, anesthetic, or another gas to the nasal passages of a user. Fitting 200 may include any suitable structure to connect multi-chamber mask 100 to gas supply source 300. For example, fitting 200 may be an acrylic, male-type hose connector that couples to an opening into multi-chamber mask 100. As another example, fitting 200 may be a gasket surrounding an opening into multi-chamber mask 100. Gas supply source 300 may be, for example, a continuous positive air pressure (CPAP) system that supplies air or another gas at a positive pressure to help open the user's breathing passage and thereby improve the user's breathing.

In certain embodiments, multi-chamber mask 100 is custom formed to fit the user's unique facial structure and features, including at least the portion of the user's face surrounding the user's mouth and nostrils. This may allow multi-chamber mask 100 to provide reduced leakage, increased comfort, and better performance.

In certain embodiments, multi-chamber mask 100 is formed from a first layer 102, a second layer 104, and a partition 106. When assembled, first layer 102, second layer 104, and partition 106 define an upper chamber and a lower chamber. In certain embodiments, first layer 102 operates to form a seal between multi-chamber mask 100 and the user's face to substantially prevent leakage of gas between multi-chamber mask 100 and the user's face. Similarly, second layer 104 is coupled to first layer 102 to substantially prevent leakage of gas between second layer 104 and first layer 102.

Multi-chamber mask 100 may be secured to the user's face in any appropriate manner. In certain embodiments, multi-chamber mask 100 may include buckles, snaps, or other devices to couple multi-chamber mask 100 to one or more straps, which may help secure multi-chamber mask 100 to the user's face during use. In certain embodiments, as described more fully below, multi-chamber mask 100 may be secured in cooperation with an oral appliance, with or without straps.

In operation, multi-chamber mask 100 may be positioned such that gas from gas supply source 300 flows through fitting 200, through the upper chamber of multi-chamber mask 100, and through the user's nasal passages to the user's breathing passage. In certain embodiments, partition 106 may substantially prevent gas from gas supply source 300 from flowing into the lower chamber of multi-chamber mask 100, thereby substantially preventing the gas from entering the mouth of the user. However, gas may flow out of the user's mouth and into the lower chamber of multi-chamber mask 100. The use of multi-chamber mask 100, having an upper chamber and a lower chamber, may allow for improved performance when multi-chamber mask 100 is used for treating sleep disordered breathing, for administering anesthesia, or for any other suitable purpose for which multi-chamber mask 100 is used.

Figure 2A:
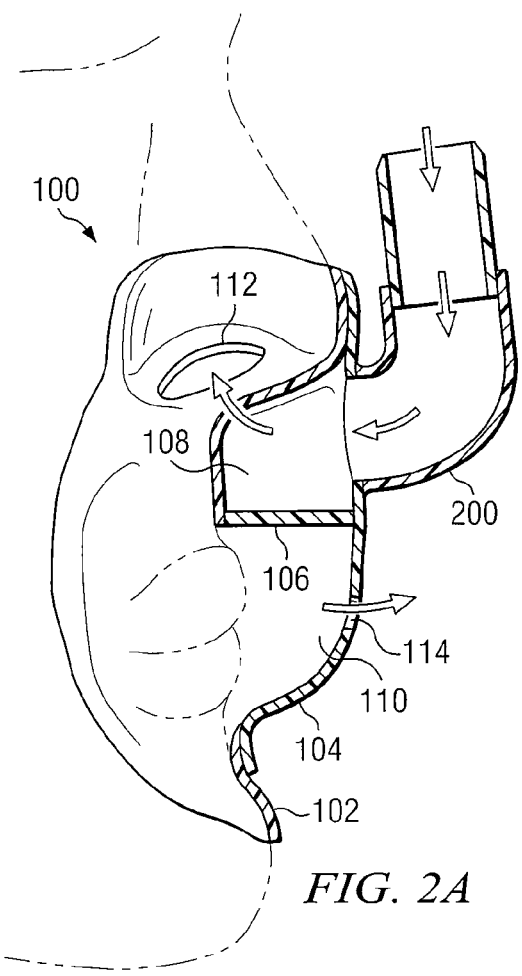
FIGS. 2A and 2B illustrate cross-sectional views of an example multi-chamber mask.
Figure 2B:
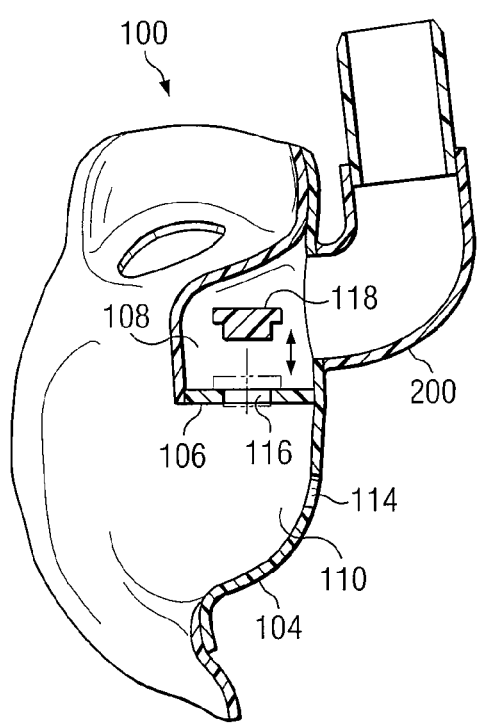

FIGS. 2A and 2B illustrate cross-sectional views of an example multi-chamber mask 100. In certain embodiments, first layer 102, second layer 104, and partition 106 cooperate to define upper chamber 108 and lower chamber 110. First layer 102 may include one or more openings 112 that allow gas to flow into the user's nostrils. In certain embodiments, upper chamber 108 may be positioned proximate the nostrils such that gas supplied by gas supply source 300 may flow through upper chamber 108 and into the nostrils. Second layer 104 may contain an opening 114 that allows gas to flow out of lower chamber 110. The size of opening 114 may vary depending on the desired flow. For example, opening 114 may have a diameter of approximately 0.25 inches. In certain embodiments, opening 114 may be used to connect multi-chamber mask 100 to forwardly extending post of an oral appliance or to provide access to an adjustment mechanism of an oral appliance.

In certain embodiments, as shown in FIG. 2B, partition 106 may include opening 116 allowing gas to flow between upper chamber 108 and lower chamber 110. The size of opening 116 may vary depending on the desired flow between upper chamber 108 and lower chamber 110. Additionally, multi-chamber mask 100 may include a removable structure 118, such as a "stopper," to selectively control the flow of gas between upper chamber 108 and lower chamber 110. Although not explicitly shown, in another embodiment, partition 106 may include a valve adapted to regulate the flow of gas between upper chamber 108 and lower chamber 110. The valve may be a single directional valve such that, for example, gas may only flow through the valve from lower chamber 110 to upper chamber 108. Alternatively, the valve may be an adjustable valve that may be adjusted to allow a prescribed flow through the valve.

Figure 3A:
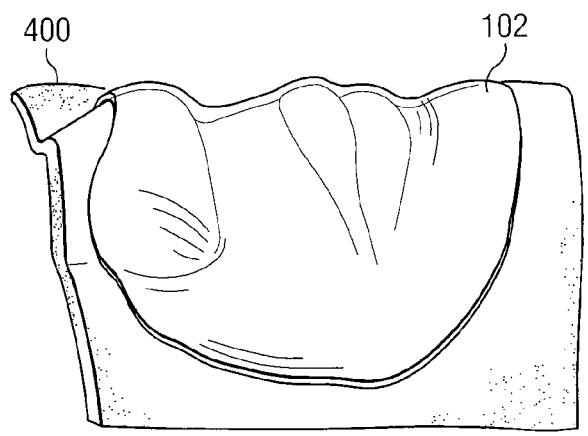
FIGS. 3A-3F illustrate an example method for forming an example multi-chamber mask.

FIGS. 3A-3F illustrate an example method for forming an example multi-chamber mask 100. As shown in FIG. 3A, first layer 102 is applied to facial surface 400. Facial surface 400 includes a contoured surface representing the features of a portion of a generic or specific user's face. For example, facial surface 400 may be a facial cast formed from plastic, plaster, stone, acrylic, or any other material suitable to represent the features of a specific user's face. As another example, facial surface 400 may be the actual surface of a specific user's face. Facial surface 400 may be prepared with a thin layer of material to reduce the tendency of first layer 102 to adhere to facial surface 400.

In certain embodiments, first layer 102 may include a deformable material such as a suitable thermoplastic polymer and any suitable fillers, stabilizers, coloring agents, antioxidants, antimicrobial agents, or other materials. In certain embodiments, first layer 102 may include a light curing material such as the material sold under the name TRIAD by DENSTSPLY INTERNATIONAL, INC. Such materials are well known in various contexts to those skilled in the art.

In one particular embodiment, first layer 102 may include, possibly in addition to one or more other materials, one or more of the polycaprolactone polymers or other aliphatic polyesters described in U.S. Pat. Nos. 4,784,123 and 5,112,225 and product literature of UNION CARBIDE CORPORATION. One or more such polycaprolactone polymers may have the formula:

(1)

where R is an aliphatic hydrocarbon and n may range between approximately 300 to approximately 650. The TONE polycaprolactone polymers are described in U.S. Pat. Nos. 4,784,123 and 5,112,225 and product literature of UNION CARBIDE CORPORATION as including homopolymers, block copolymers, graft copolymers, or other polymers containing epsilon-caprolactone. Polymerization may be initiated using a diol, for example and without limitation, ethylene glycol, diethylene glycol, neopentyl glycol, butane diol, hexane diol, or any other appropriate diol. The diol may have the formula:

(2)

where R is an aliphatic hydrocarbon. Where first layer 102 includes one or more polycaprolactone polymers, any suitable polycaprolactone polymer or polymers may be used. In general, polycaprolactone polymers may display desirable dimensional stability and thermoplasticity during cooling, biocompatibility, and a variety of other characteristics making them suitable for use in forming first layer 102, as described herein.

In another particular embodiment, first layer 102 may begin as a thin sheet of deformable material that is substantially flat except for one or more depressions such as a depression sufficient to accommodate a generic user's nose, including at least the portion of the generic user's nose surrounding the user's nostrils. Alternatively, first layer 102 may begin as a thin sheet of deformable material that is substantially flat over its entire surface and does not include any depressions. Thin sheets of an appropriate deformable material may be obtained, for example, from CHESAPEAKE MEDICAL PRODUCTS, INC. In all cases, first layer 102 may include pre-formed holes positioned according to the position of a generic user's nostrils. First layer 102 may be formed using an injection molding process (i.e., deformable material is placed into an injection molding machine while in a liquid state), using a pressing process (i.e., deformable material is placed into a press while in a deformable state), or using any other suitable technique. First layer 102 may be sized for various classes of generic users, for example, large for men, medium for women, and small for children. In one embodiment, first layer 102 may be mass produced quickly, inexpensively, and with high quality and uniformity.

Prior to applying first layer 102 to facial surface 400, first layer 102 is placed in a deformable state. For example, where first layer 102 includes one or more polycaprolactone polymers, first layer 102 may be heated in a microwave oven, in water or other non-solvent neutral liquid, or in any other suitable manner to between approximately 140° F. and approximately 180° F. so as to place first layer 102 in a deformable state. While in a deformable state, first layer 102 is brought in contact with facial surface 400, including at least the portion of facial surface 400 corresponding to the area surrounding the user's mouth and nostrils. First layer 102 is then pressed against or otherwise allowed to conform to the shape of facial surface 400. As the deformable material cools and hardens, first layer 102 solidifies and will substantially retain the shape of facial surface 400.

Figure 3B:
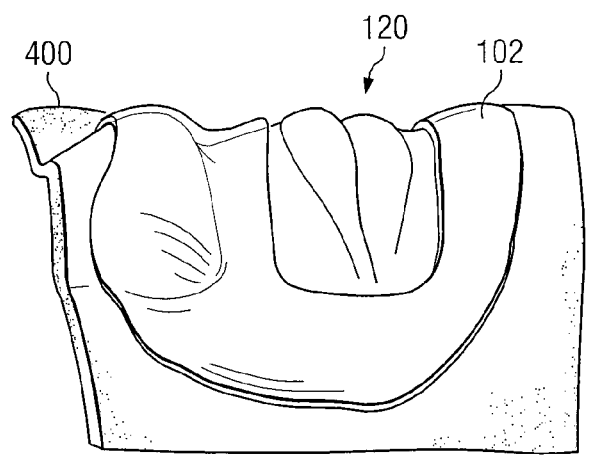

As shown in FIG. 3B, in certain embodiments, a portion of first layer 102 corresponding to the user's mouth may be removed to form opening 120. The removal of this portion of first layer 102 may be performed prior to or following application of first layer 102 to facial surface 400. The removal of this portion of first layer 102 may also be performed before, during, or after first layer of thin material is placed in a deformable state. Alternatively, rather than removing a portion of first layer 102 to form opening 120, first layer 102 may be initially formed having opening 120 such that no material needs to be removed.

In certain embodiments, first layer 102 may have portions corresponding to the user's nostrils removed to form one or more nostril openings 112. Similar to the removal of the portion corresponding to the user's mouth described above, the removal of these portions of first layer 102 may be performed prior to or following application of first layer 102 to facial surface 400. The removal of these portions may also be performed before, during, or after first layer 102 is placed in a deformable state. Alternatively, rather than removing these portions to form one or more nostril openings 112, first layer 102 may be initially formed having one or more nostril openings 112 such that no material needs to be removed.

Figure 3C:
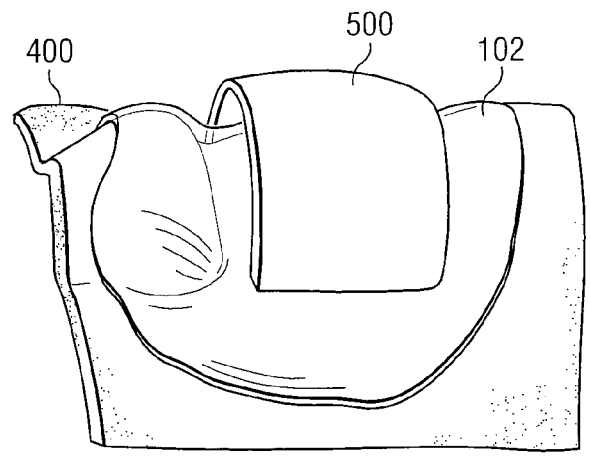

As shown in FIG. 3C, a spacer 500 may be positioned relative to first layer 102 and facial surface 400 to model the area associated with upper chamber 108 and lower chamber 110.

Figure 4A:
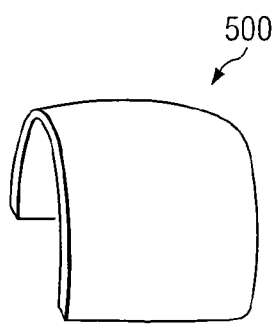
FIGS. 4A and 4B illustrate example spacers used to form an example multi-chamber mask.

FIG. 4A illustrates example spacer 500 used to form an example multi-chamber mask 100. Spacer 500 may include one or more recesses to accommodate certain features of facial surface 400, such as the features corresponding to the user's nose and mouth. Spacer 500 may be made of plastic, clay, metal, or any other appropriate material capable of being formed in the shape of the desired upper chamber 108 and lower chamber 110. Additionally, spacer 500 may be solid or formed from a thin sheet of material.

Figure 4B:
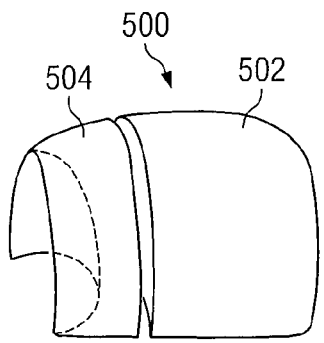

FIG. 4B illustrates an alternative example of spacer 500 used to form multi-chamber mask 100. In certain embodiments, spacer 500 may include first portion 502 and second portion 504. In this embodiment, spacer 500 may be adapted to position partition 106 relative to first layer 102, prior to application of second layer 104. In another embodiment, first portion 502 and second portion 504 may serve as a mold adapted to form partition 106. In this embodiment, first portion 502 and second portion 504 may be positioned such that the gap between first portion 502 and second portion 504 defines the desired thickness of partition 106. After first portion 502 and second portion 504 are positioned, the gap may be filled in any suitable manner with a deformable material such as a suitable thermoplastic polymer to form partition 106.

Figure 3D:
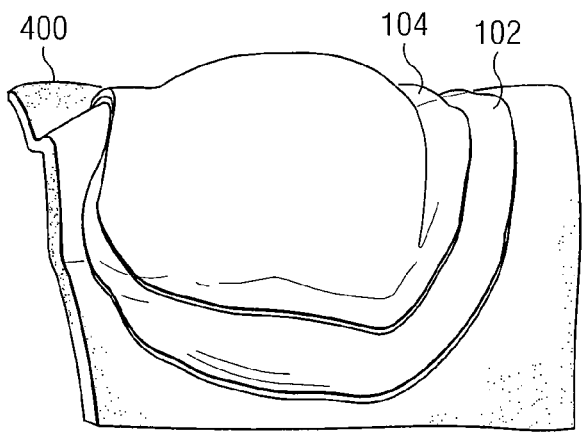

As shown in FIG. 3D, second layer 104 may be applied over spacer 500, with spacer 500 positioned relative to first layer 102 and facial surface 400. Second layer 104 may include any materials and may be formed in any manner described above with respect to first layer 102. In certain embodiments, first layer 102 and second layer 104 may be formed from the same material.

In certain embodiments, prior to applying second layer 104 to cover spacer 500 and at least a portion of first layer 102, second layer 104 is placed in a deformable state. For example, where the deformable material of second layer 104 includes one or more polycaprolactone polymers, second layer 104 may be heated in a microwave oven, in water or other non-solvent neutral liquid, or in any other suitable manner to between approximately 140° F. and approximately 180° F. so as to place second layer 104 in a deformable state. While in a deformable state, second layer 104 is brought in contact with spacer 500 and first layer 102. Second layer 104 is then pressed against or otherwise allowed to conform to the shape of spacer 500 and first layer 102. As the deformable material cools and hardens, second layer 104 solidifies and will substantially retain the shape of at least a portion of spacer 500 and first layer 102.

Figure 3E:
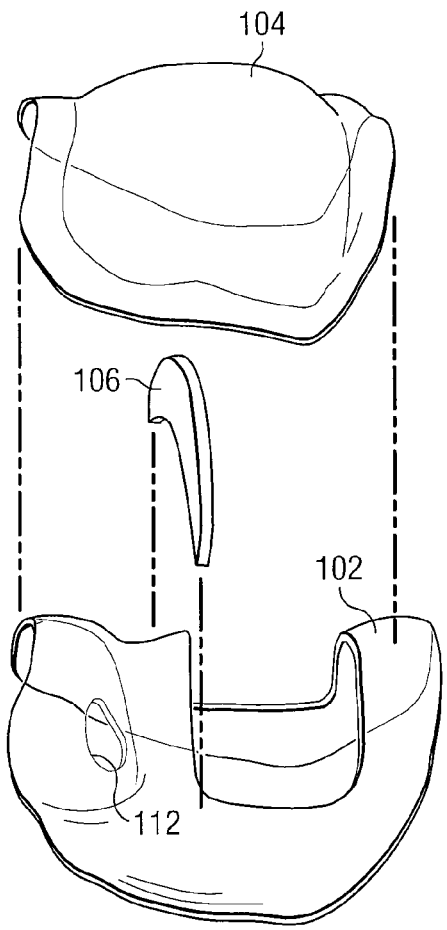

As shown in FIG. 3E, partition 106 is placed between first layer 102 and second layer 104. Partition 106 represents a dividing structure adapted to separate upper chamber 108 from lower chamber 110 to prevent or regulate the flow of gas between upper chamber 108 and lower chamber 110. Partition 106 may include a layer of thin material or any other structure suitable to separate upper chamber 108 from lower chamber 110. For example, partition 106 may include the same or similar material as first layer 102, second layer 104, or both. In a particular embodiment, partition 106 may be made of an acrylic material. Although primarily described as a separate structure, partition 106 may be formed integrally with second layer 104.

In certain embodiments, partition 106 may be positioned between the portions of multi-chamber mask 100 corresponding to a user's nostrils and mouth. Following assembly, partition 106, together with first layer 102 and second layer 104, defines upper chamber 108 and lower chamber 110. The components of multi-chamber mask 100 may be assembled and coupled to one another using a suitable adhesive or any other suitable method. For example, a suitable deformable thermoplastic material may be placed in a deformable state and applied to the areas of contact between first layer 102, second layer 104, and partition 106. The deformable thermoplastic material may then be allowed to harden, thereby fusing, bonding, or otherwise coupling first layer 102, second layer 104, and partition 106.

In certain embodiments, a portion of second layer 104 may be removed to form an opening in a position corresponding to the desired location of fitting 200. The removal of this portion of second layer 104 may be performed prior to or following the application of second layer 104 to cover spacer 500 and at least a portion of first layer 102. The removal of this portion of second layer 104 may also be performed prior to or following the assembly of multi-chamber mask 100. The opening may be positioned in any location suitable to allow gas from gas supply source 300 to flow through fitting 200 into upper chamber 108. Fitting 200 may then be affixed to second layer 104, such that fitting 200 fits into or around this opening in second layer 104.

Figure 3F:
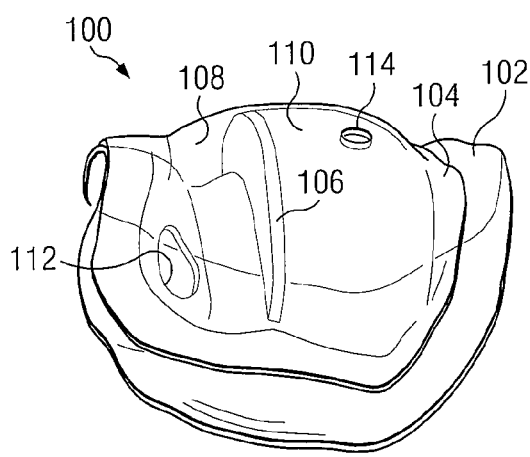

FIG. 3F illustrates the assembled components of an example multi-chamber mask 100.

Figure 5:
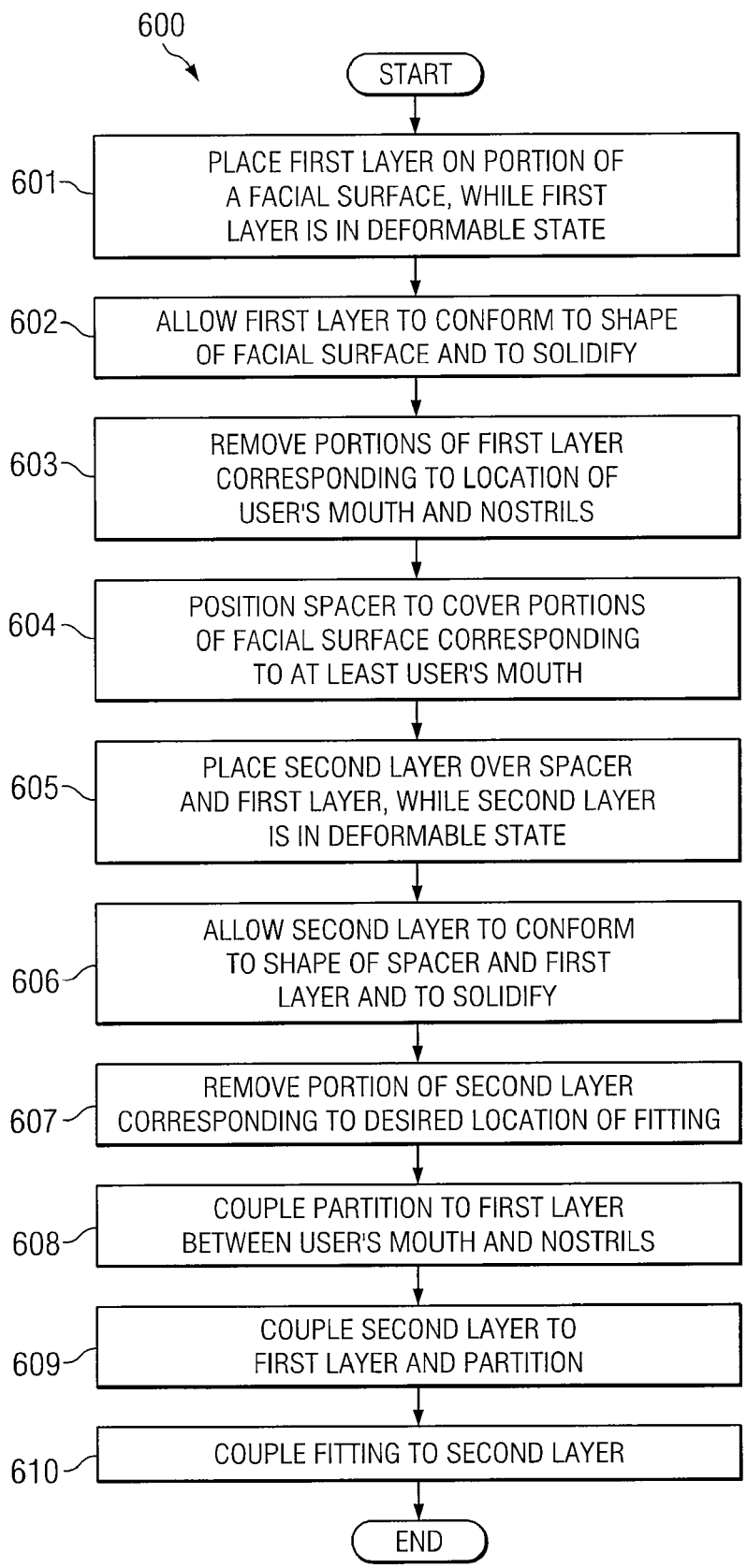
FIG. 5 is a flowchart illustrating an example method for forming an example multi-chamber mask.

FIG. 5 is a flowchart illustrating an example method 600 for forming an example multi-chamber mask 100. At step 601, first layer 102 is placed on a portion of facial surface 400, while first layer 102 is in a deformable state. At step 602, first layer 102 is allowed to conform to the shape of facial surface 400 and to solidify. At step 603, the portions of first layer 102 corresponding to the user's mouth and nostrils are removed, if not already removed before or in connection with steps 601 and 602. At step 604, spacer 500 is positioned relative to first layer 102 and facial surface 400, such that spacer 500 covers the portions of facial surface 400 corresponding to at least the user's mouth. At step 605, second layer 104 is placed over spacer 500 and at least a portion of first layer 102, while second layer 104 is in a deformable state. At step 606, second layer 104 is allowed to conform to the shape of spacer 500 and first layer 102 and to solidify. At step 607, a portion of second layer 104 corresponding to the desired location of fitting 200 may be removed, if not already removed before or in connection with steps 605 and 606. At step 608, partition 106 is coupled to first layer 102 between the user's mouth and nostrils. At step 609, second layer 104 is coupled to first layer 102 and partition 106. As described above, in certain embodiments, steps 608 and 609 may be performed substantially simultaneously. At step 610, fitting 200 is coupled to second layer 104.

Although the present invention has been described in several embodiments, a plenitude of modifications may be suggested to one skilled in the art, and it is intended that the present invention encompass such modifications as fall within the scope of the appended claims.

What is claimed is:

1. A multi-chamber mask, comprising:
a shell adapted to cover portions of a user's face comprising the user's mouth and at least portions of the user's nose comprising the nostrils, the shell comprising a custom-fit contact surface custom-shaped according to portions of the user's face surrounding the covered portions of the user's face, the custom-fit contact surface preventing gas from escaping between the shell and the contacted portions of the user's face, the shell adapted to couple to a gas supply source; and
a partition coupled to the shell between first and second layers of the shell, the partition cooperating with the shell to define a first chamber and a second chamber, the first layer custom-shaped according to at least a portion of the user's nose comprising the nostrils, the first layer defining an inner boundary of the first chamber, the first chamber adapted to be positioned proximate the user's nose to direct inflow of gas from a gas supply source to the user's nasal passages through one or more openings in the first layer, the second chamber adapted to be positioned proximate the user's mouth, the partition preventing flow of gas from the first chamber to the second chamber.

2. The multi-chamber mask of claim 1, wherein the first layer prevents gas from escaping between the first layer and the contacted portions of the user's face; and
wherein the second layer is coupled to the first layer and the second layer prevents gas from escaping between the first and second layers.

3. The multi-chamber mask of claim 1, wherein the shell comprises an opening adapted to allow gas to flow out of the mask from the second chamber.

4. The multi-chamber mask of claim 1, wherein the shell comprises an opening adapted to couple to a post of an oral appliance.

5. The multi-chamber mask of claim 1, wherein the partition comprises an opening adapted to allow gas to flow between the first chamber and the second chamber.

6. The multi-chamber mask of claim 1, wherein the shell comprises a thermoplastic polymer.

7. The multi-chamber mask of claim 6, wherein the thermoplastic polymer comprises a polycaprolactone polymer.

8. The multi-chamber mask of claim 1, wherein the shell has been custom-formed to fit the user's unique facial features.

9. A method of forming a multi-chamber mask, comprising:
providing a shell comprising a custom-fit contact surface custom-shaped according to physical features of a user's face comprising the area corresponding to the user's mouth and at least a portion of the user's nose comprising the nostrils; and
providing a partition coupled to the shell between first and second layers of the shell, the partition cooperating with the shell to define a first chamber and a second chamber, the first layer custom-shaped according to the contour of at least a portion of the user's nose comprising the nostrils, the first layer defining an inner boundary of the first chamber, the first chamber adapted to be positioned proximate the user's nose to direct inflow of gas from a gas supply source to the user's nasal passages through one or more openings in the first layer, the second chamber adapted to be positioned proximate the user's mouth, the partition preventing flow of gas from the first chamber to the second chamber.

10. The method of claim 9, wherein the first layer substantially prevents gas from escaping between the first layer and the contacted portions of the user's face; and
wherein the second layer is coupled to the first layer and the second layer to substantially prevents gas from escaping between the first and second layers.

11. The method of claim 9, further comprising coupling a fitting to the shell, the fitting adapted to couple the multi-chamber mask to the gas supply source.

12. The method of claim 9, further comprising providing an opening in the shell adapted to allow gas to flow out of the mask from the second chamber.

13. The method of claim 9, further comprising providing an opening in the partition adapted to allow gas to flow between the first chamber and the second chamber.

14. The method of claim 9, wherein the shell comprises a thermoplastic polymer.

15. The method of claim 14, wherein the thermoplastic polymer comprises a polycaprolactone polymer.

16. A method of forming a multi-chamber mask, comprising:
providing a first layer of deformable material covering portions of a facial surface, the facial surface representing physical features of a user's face, the covered portions of the facial surface comprising portions corresponding to the user's mouth and at least a portion of the user's nose comprising the nostrils;

providing one or more openings in the first layer of deformable material corresponding to the user's nostrils;

providing one or more spacers covering at least a portion of the facial surface corresponding to the user's mouth;

providing a second layer of deformable material over the one or more spacers and at least a portion of the first layer;

providing a partition between the first and second layers of deformable material adapted to cooperate with the first and second layers of deformable material to define a first chamber and a second chamber, the first chamber adapted to be positioned proximate the user's nose to direct inflow of gas from a gas supply source to the user's nasal passages, the second chamber adapted to be positioned proximate the user's mouth to restrict outflow of gas from the user's mouth in response to inflow of gas from the gas supply source to the user's nasal passages, the partition adapted to restrict flow of gas between the first and the second chamber; and coupling the first layer of deformable material to the second layer of deformable material, with the partition between the first and second layers of deformable material, to form the multi-chamber mask.

17. The method of claim 16, wherein the one or more openings in the first layer are formed before the first layer is positioned to cover portions of the facial surface.

18. The method of claim 16, wherein one or more of the first layer, the second layer, and the partition comprise a thermoplastic polymer.

19. The method of claim 16, wherein one or more of the first layer, the second layer, and the partition comprise a polycaprolactone polymer.

20. A method of forming a multi-chamber mask, comprising:

providing a shell covering portions of a facial surface, the facial surface representing physical features of a user's face, the facial surface comprising a cast of a portion of the user's face, the covered portions comprising the area corresponding to the user's mouth and at least a portion of the user's nose comprising the nostrils; and providing a partition coupled to the shell between first and second layers of the shell, the partition cooperating with the shell to define a first chamber and a second chamber, the first chamber adapted to be positioned proximate the user's nose to direct inflow of gas from a gas supply source to the user's nasal passages through one or more openings in the first layer, the second chamber adapted to be positioned proximate the user's mouth to restrict outflow of gas from the user's mouth in response to inflow of gas from the gas supply source to the user's nasal passages, the partition adapted to restrict flow of gas between the first and the second chamber.

21. A multi-chamber mask, comprising:

a shell adapted to cover portions of a user's face comprising the user's mouth and at least portions of the user's nose comprising the nostrils, the shell comprising a contact surface corresponding to portions of the user's face surrounding the covered portions of the user's face, the contact surface comprising a shape that substantially restricts gas from escaping between the shell and the contacted portions of the user's face, the shell adapted to couple to a gas supply source; and a partition coupled to the shell between first and second layers of the shell, the partition cooperating with the shell to define a first chamber and a second chamber, the first chamber adapted to be positioned proximate the user's nose to direct inflow of gas from a gas supply source to the user's nasal passages, the second chamber adapted to be positioned proximate the user's mouth, the partition preventing flow of gas from the first chamber to the second chamber;

wherein the first layer comprises one or more openings adapted to be positioned below one or more of the user's nostrils to direct the inflow of gas from the gas supply source to the user's nasal passages.

22. The multi-chamber mask of claim 21, wherein the first layer comprises the contact surface and is configured such that gas is substantially prevented from escaping between the first layer and the contacted portions of the user's face; and wherein the second layer is coupled to the first layer and configured such that gas is substantially prevented from escaping between the first and second layers.

23. The multi-chamber mask of claim 21, wherein the shell comprises an opening adapted to allow gas to flow out of the mask from the second chamber.

24. The multi-chamber mask of claim 21, wherein the shell comprises an opening adapted to couple to a post of an oral appliance.

25. The multi-chamber mask of claim 21, wherein the partition comprises an opening adapted to allow gas to flow between the first chamber and the second chamber.

26. The multi-chamber mask of claim 21, wherein the shell comprises a thermoplastic polymer.

27. The multi-chamber mask of claim 26, wherein the thermoplastic polymer comprises a polycaprolactone polymer.

28. The multi-chamber mask of claim 21, wherein the shell has been custom-formed to fit the user's unique facial features.

29. A method of forming a multi-chamber mask, comprising:

providing a shell comprising a custom-fit surface custom-shaped according to physical features of a user's face comprising the area corresponding to the user's mouth and at least a portion of the user's nose comprising the nostrils; and providing a partition coupled to the shell between first and second layers of the shell, the partition cooperating with the shell to define a first chamber and a second chamber, the first chamber adapted to be positioned proximate the user's nose to direct inflow of gas from a gas supply source to the user's nasal passages through one or more openings in the first layer, the one or more openings adapted to be positioned below one or more of the user's nostrils, the second chamber adapted to be positioned proximate the user's mouth, the partition preventing flow of gas from the first chamber to the second chamber.

30. The method of claim 29, wherein the first layer is adapted to contact the user's face to substantially prevent gas from escaping between the first layer and the contacted portions of the user's face;

wherein the second layer adapted to couple to the first layer to substantially prevent gas from escaping between the first and second layers.

31. The method of claim 29, further comprising coupling a fitting to the shell, the fitting adapted to couple the multi-chamber mask to the gas supply source.

32. The method of claim 29, further comprising providing an opening in the shell adapted to allow gas to flow out of the mask from the second chamber.

33. The method of claim 29, further comprising providing an opening in the partition adapted to allow gas to flow between the first chamber and the second chamber.

34. The method of claim 29, wherein the shell comprises a thermoplastic polymer.

35. The method of claim 34, wherein the thermoplastic polymer comprises a polycaprolactone polymer.

36. A multi-chamber mask, comprising:
   a shell adapted to cover portions of a user's face comprising the user's mouth and at least portions of the user's nose comprising the nostrils, the shell adapted to contact the user's face surrounding the covered portions of the user's face to substantially prevent gas from escaping between the shell and the contacted portions of the user's face, the shell adapted to couple to a gas supply source; and
   a partition coupled to the shell between first and second layers of the shell, the partition cooperating with the shell to define a first chamber and a second chamber, the first chamber adapted to be positioned proximate the user's nose to direct inflow of gas from the gas supply source to the user's nasal passages through one or more openings in the first layer of the shell, the second chamber adapted to be positioned proximate the user's mouth to restrict outflow of gas from the user's mouth in response to inflow of gas from the gas supply source to the user's nasal passages, the partition adapted to restrict flow of gas between the first and the second chamber;
   wherein the shell comprises a thermoplastic polymer that has been custom-formed to fit the user's unique facial features.

37. The multi-chamber mask of claim 36, wherein the first layer is adapted to contact the user's face to substantially prevent gas from escaping between the first layer and the contacted portions of the user's face; and
   wherein the second layer is adapted to couple to the first layer to substantially prevent gas from escaping between the first and second layers.

38. The multi-chamber mask of claim 36, wherein the shell comprises an opening adapted to allow gas to flow out of the mask from the second chamber.

39. The multi-chamber mask of claim 36, wherein the shell comprises an opening adapted to couple to a post of an oral appliance.

40. The multi-chamber mask of claim 36, wherein the partition comprises an opening adapted to allow gas to flow between the first chamber and the second chamber.

41. The multi-chamber mask of claim 36, wherein the thermoplastic polymer comprises a polycaprolactone polymer.

* * * * *